United States Patent
Ishii et al.

(10) Patent No.: US 8,530,699 B2
(45) Date of Patent: Sep. 10, 2013

(54) PROCESS FOR PRODUCTION OF (METH) ACRYLIC ACID

(75) Inventors: Yoshitake Ishii, Himeji (JP); Koji Ueno, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 13/266,672
(22) PCT Filed: May 7, 2010
(86) PCT No.: PCT/JP2010/057815
§ 371 (c)(1), (2), (4) Date: Oct. 27, 2011
(87) PCT Pub. No.: WO2010/134434
PCT Pub. Date: Nov. 25, 2010

(65) Prior Publication Data
US 2012/0046495 A1 Feb. 23, 2012

(30) Foreign Application Priority Data
May 19, 2009 (JP) ................................. 2009-120623

(51) Int. Cl.
C07C 51/42 (2006.01)
(52) U.S. Cl.
USPC ........................................................ 562/600
(58) Field of Classification Search
None
See application file for complete search history.

(56) References Cited

U.S. PATENT DOCUMENTS

| | | | | |
|---|---|---|---|---|
| 6,596,901 | B1 * | 7/2003 | Eck et al. ................. | 562/600 |
| 7,803,969 | B2 | 9/2010 | Nordhoff et al. | |
| 7,964,689 | B2 | 6/2011 | Nordhoff et al. | |
| 2004/0116741 | A1 | 6/2004 | Nordhoff et al. | |
| 2011/0028664 | A1 | 2/2011 | Nordhoff et al. | |

FOREIGN PATENT DOCUMENTS

| | | |
|---|---|---|
| JP | 2000-514077 | 10/2000 |
| JP | 2004-535360 | 11/2004 |
| WO | 2007/088981 | 8/2007 |
| WO | 2007088981 | * 8/2007 |

OTHER PUBLICATIONS

"Crystallization" in Kirk-Othmer Encyclopedia of Chemical Technology, Joachim Ulrich and Torsten Stelzer, Copyright © 2001 by John Wiley & Sons, Inc; pp. 1-63.*
International Search Report issued Jun. 10, 2010 in International (PCT) Application No. PCT/JP2010/057815, of which the present application is the national stage.
Fisher et al., Crystallization Without Solvent, Chemical Engneering World, vol. 34, No. 1, pp. 79-81 and 84, Jan. 1999.
Office Action issued Apr. 25, 2013 in corresponding Chinese Application No. 201080009469.1, with English translation.

* cited by examiner

Primary Examiner — Karl J Puttlitz
(74) Attorney, Agent, or Firm — Wenderoth, Lind & Ponack, L.L.P.

(57) ABSTRACT

The objective of the present invention is to provide a process for producing highly pure (meth) acrylic acid stably and efficiently with crystallization. The process for production of (meth)acrylic acid according to the present invention is characterized in comprising the steps of cooling a crude (meth) acrylic acid solution in a crystallization apparatus until the temperature of a cooling medium discharged from the crystallization apparatus is stabilized in the range of higher than the solidification point of the crude (meth)acrylic acid solution in the crystallization apparatus and not more than the solidification point plus 5° C.; then bringing the crude (meth) acrylic acid solution in the crystallization apparatus to a supercooled condition by setting the temperature of a cooling medium supplied to the crystallization apparatus at the temperature of not more than the solidification point of the crude (meth)acrylic acid solution minus 1° C.; and crystallizing (meth)acrylic acid from the crude (meth)acrylic acid solution.

4 Claims, 1 Drawing Sheet

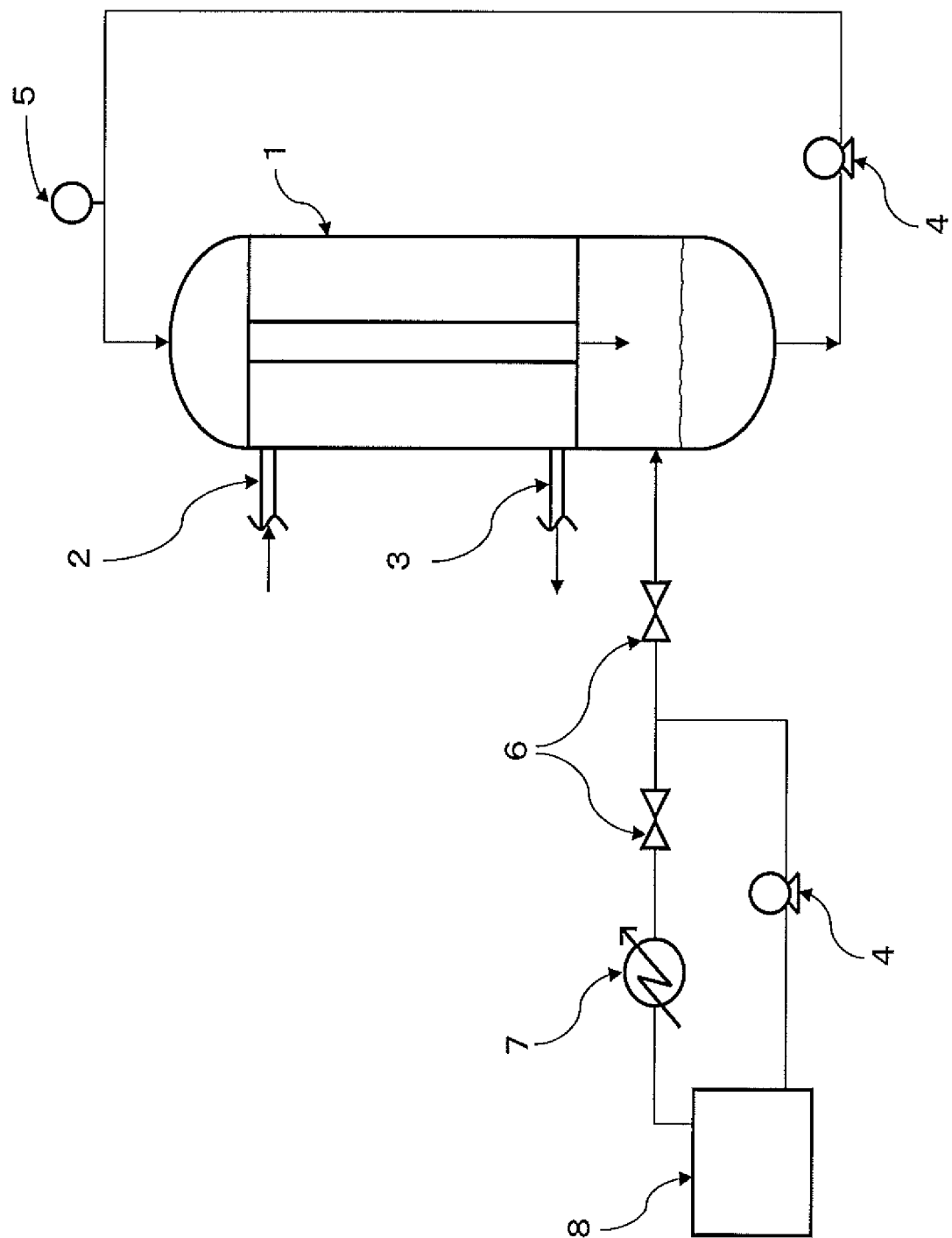

PROCESS FOR PRODUCTION OF (METH) ACRYLIC ACID

TECHNICAL FIELD

The present invention relates to a process for production of (meth)acrylic acid.

BACKGROUND ART (Meth)acrylic acid is generally produced by carrying out a gas-phase catalytic oxidation reaction to obtain a gas containing (meth)acrylic acid, supplying the gas into a condensation tower or a collection tower to obtain a crude (meth)acrylic acid solution, and purifying (meth)acrylic acid from the crude solution. As such a purification procedure, crystallization in addition to distillation, diffusion, extraction and others are exemplified.

It has been known that the purity and the condition of a crystal depend on a cooling rate and cooling time during crystallization. A general crystallization is carried out by cooling a crude solution to less than the solidification point. Nevertheless, especially in a large-scale industrial production of (meth)acrylic acid, the temperature during crystallization has not been necessarily controlled rigorously.

For example, Patent Document 1 discloses a process for obtaining highly pure (meth)acrylic acid more easily, wherein the gas which contains (meth) acrylic acid and which is obtained by a gas-phase catalytic oxidation is condensed, and (meth)acrylic acid is crystallized from the obtained solution. The temperature range for crystallization is exemplified by −25° C. to +14° C. and 12° C. to −5° C. In the Example described in the Patent Document 1, the first acrylic acid crystal was formed by cooling a crude solution from room temperature to −0.9° C., and the mixture was further cooled to −4.4° C. over 3 hours and 54 minutes. However, there is no detailed description about the change of a crude solution temperature from a relatively high temperature of the crude solution up to the temperature at which acrylic acid was crystallized. It is believed that said temperature was not the temperature of the crude solution but was the jacket temperature of the crystallization apparatus, since there is some technical uncertainty that the crude solution temperature was lowered down to −0.9° C. whereas the melting point of acrylic acid is 13.5° C.

In addition, Patent Document 2 discloses a process, wherein a crystal is precipitated before crystallization step by preliminarily cooling a crude solution down to not more than the solidification temperature, and then, a mixture of the crystal and the crude solution is supplied to a crystallization tank. It is described that, according to the process, scale formation in the crystallization tank can be suppressed and a coarse particle with superior filterability can be obtained. In the Example described in the Patent Document 2, a crude solution having the solidification point of 8.5° C. was preliminarily cooled to 8.3° C., and the produced crystal was supplied to a crystallization tank with the crude solution. However, the process is characterized in obtaining a crystal in advance before a crude solution is supplied into a crystallization tank, and there is no consideration of the purity of a crystal and the like.

PRIOR ART

Patent Document

Patent Document 1: JP2000-514077T
Patent Document 2: WO2007/088981

DISCLOSURE OF THE INVENTION

Problems to be Solved by the Invention

As mentioned above, it has been conventionally and generally carried out that (meth)acrylic acid is crystallized for purification. However, there has been no rigorous investigation of controlling the temperature during crystallization in the production of (meth)acrylic acid, though the crystal quality depends on a cooling condition. It is therefore difficult that highly pure (meth)acrylic acid is stably and efficiently obtained from a crude (meth) acrylic acid solution in which many impurities are included and of which components vary drastically depending on a reaction condition.

The objective of the present invention is to provide a process for producing highly pure (meth) acrylic acid stably and efficiently with crystallization procedure.

Means for Solving the Problems

The present inventors engaged in diligent research to solve the above-described problem. As a result, the present inventors found that more highly pure (meth)acrylic acid can be stably obtained under the following conditions, and completed the present invention:

a crude (meth)acrylic acid solution is cooled to the extent where a crystal does not precipitate before the solution is cooled down to not more than the solidification point for crystallization; and then, the crude solution is brought to a clear supercooled condition by cooling down to less than the solidification point.

The process for production of (meth)acrylic acid according to the present invention is characterized in comprising the steps of:

cooling a crude (meth)acrylic acid solution in a crystallization apparatus until the temperature of a cooling medium discharged from the crystallization apparatus is stabilized in the range of higher than the solidification point of the crude (meth)acrylic acid solution in the crystallization apparatus and not more than the solidification point plus 5° C.;

then bringing the crude (meth)acrylic acid solution in the crystallization apparatus to a supercooled condition by setting the temperature of a cooling medium supplied to the crystallization apparatus to be lower than the solidification point of the crude (meth)acrylic acid solution by not less than 1° C.; and crystallizing (meth)acrylic acid from the crude (meth) acrylic acid solution.

In the present invention process, it is preferred that the temperature of the cooling medium which is supplied to the crystallization apparatus and which is used for bringing the crude (meth)acrylic acid solution to a supercooled condition is set to be lower than the solidification point of the crude (meth)acrylic) acrylic acid solution by not less than 1° C. and yet not more than 10° C. When a crude (meth)acrylic acid solution is cooled with a cooling medium of excessively low temperature for a short time, crystallization may proceed rapidly after supercooling and the purity of a crystal may possibly be reduced. On the other hand, when the temperature of the cooling medium is set to be lower than the solidification point of the crude (meth)acrylic acid solution by not less than 1° C. and yet not more than 10° C., the crude solution is not excessively supercooled and a highly pure crystal can be obtained more reliably.

In the method of the present invention, it is preferred to use a falling liquid film type crystallization apparatus as a crystallization apparatus. In a falling liquid film type crystallization apparatus, it is easier that the cool energy of a cooling medium is efficiently transferred to a crude (meth)acrylic acid solution through a heat-transfer surface, and temperature control of the crude solution is easy. Therefore, a highly pure crystal can be easily obtained using a falling liquid film type crystallization apparatus.

BRIEF DESCRIPTION OF DRAWINGS

FIG. 1 is a diagrammatic illustration showing one embodiment of a crystallization apparatus used in the present invention process. In the FIGURE, "1" is a crystallization apparatus, "2" is a cooling medium inlet, "3" is a cooling medium outlet, "4" is a pump, "5" is a pressure gauge, "6" is a valve, "7" is a heat exchanger, and "8" is a crude (meth) acrylic acid solution tank.

MODE FOR CARRYING OUT THE INVENTION

The present invention process is described as the above. Hereinafter, the present invention process is explained in detail according to the implementation sequence.

1. Preliminary Cooling Step

In the present invention process, first, a crude (meth)acrylic acid solution in a crystallization apparatus is cooled until the temperature of a cooling medium discharged from the crystallization apparatus is stabilized in the range of higher than the solidification point of the crude (meth)acrylic acid solution in the crystallization apparatus and not more than the solidification point plus 5° C.

A crude (meth)acrylic acid solution is not particular limited as long as it contains impurity in addition to (meth)acrylic acid as the target compound. For example, the crude (meth)acrylic acid solution prepared by carrying out a gas-phase catalytic oxidation reaction to obtain a gas containing (meth)acrylic acid and contacting the gas with a collecting liquid or condensating the gas can be used. The crude (meth)acrylic acid solution obtained by contacting a gas containing (meth)acrylic acid with a collecting liquid or condensing the gas includes by-product impurity such as water, acetic acid, propionic acid, maleic acid, acetone, acrolein, furfural and formaldehyde, in addition to (meth)acrylic acid and a unreacted raw material.

In order to obtain higher purity (meth)acrylic acid, a crystallization purification may be repeated two or more times. Specifically, once (meth)acrylic acid may be purified by crystallization, and the purified (meth)acrylic acid may be melted to be supplied to a crystallization apparatus in place of a crude (meth)acrylic acid solution for crystallization. In the present invention, in the case where a crystallization purification is repeated two or more times, the (meth)acrylic acid which is purified one or more times and is further crystallized is also referred to as "a crude solution" when the (meth)acrylic acid is further crystallized.

In the present invention process, the kind of a crystallization apparatus used for a crystallization purification of (meth)acrylic acid is not particularly limited. For example, it is preferable to use a crystallization apparatus that employs dynamic crystallization, such as a falling liquid film type and a full-flow tube type. In such a apparatus, the cooling energy of a cooling medium is readily transferred to a crude (meth)acrylic acid solution via a heat-transfer surface of the crystallization apparatus, and it is easier to control the temperature of said crude solution. In particular, a falling liquid film type crystallization apparatus is suitable since it is possible that the clogging of a pipe and the pressure increases of a crude solution which accompany the progression of crystallization can be inhibited.

FIG. 1 shows an example of a dynamic crystallization apparatus used in the present invention process. Of course, the present invention is not limited to the embodiment in any way.

By the crystallization apparatus shown in FIG. 1, a crude (meth)acrylic acid solution can be circulated and the temperature thereof can be controlled to crystallize (meth)acrylic acid. Specifically, a crude (meth)acrylic acid solution to be supplied to a falling liquid film type crystallization apparatus 1 is supplied from the top part of a crystallization apparatus 1 using a pump 4. The supplied crude solution falls down the interior side of a crystallization tube inside the crystallization apparatus. A crystallization tube is not limited, but is generally constituted from a material with superior corrosion-resistance and good thermal conductivity, such as stainless steel and copper. In addition, there is a heating medium or a cooling medium outside a crystallization tube, and a heating energy or a cooling energy of a medium is transferred to a crude solution inside the crystallization tube through a heat-transfer surface. The temperature of a crude solution stored in a tank 8 may be controlled with a heat exchanger 7 prior to being supplied to a crystallization apparatus 1. Alternatively, a crude solution stored in a tank 8 may be directly supplied to a crystallization apparatus 1, and the temperature thereof may be controlled inside the crystallization apparatus 1. The temperature of the crude solution stored in a tank 8 is preferably controlled in the range of not less than +3° C. and not more then +20° C. of the solidification point thereof, since cooling within a crystallization apparatus 1 invests time and productivity is decreased when the temperature is too high. Such a temperature control can be carried out using a valve 6.

A crystallization apparatus 1 is constituted such that the heat from a heating energy or a cooling energy of a medium is adequately transferred to a crude (meth)acrylic acid. For example, it is proffered that the surface area of a heat-transfer surface is increased by elongating the crystallization tubes of a crystallization apparatus 1. For example, the surface area of a heat-transfer surface can be sufficiently large by setting a crystallization tube to have a diameter in the range of not less than 50 mm and not more than 100 mm and a length in the range of not less than 15 m and not more than 25 m. The number of a crystallization tube may be one. On the other hand, the number may be two or more so that the surface area of a heat-transfer surface can be relatively larger.

In the present invention process, a crude solution is cooled in a crystallization apparatus so that the temperature becomes as low as possible without precipitating (meth)acrylic acid before (meth)acrylic acid is crystallized from the crude solution. Such a step makes it possible for the crude solution to be in a clear supercooled state in the next step.

The solidification point of a crude (meth)acrylic acid solution can be measured by a preliminary experiment and others. Specifically, a portion of a crude solution is collected and gradually cooled, and the temperature at which a crystal is produced can be determined as the solidification point. The solidification point may be lower than the melting point of (meth)acrylic acid, since the solution derived from a gas-phase catalytic oxidation reaction contains an impurity. The melting point of acrylic acid is 13.5° C., and the melting point of methacrylic acid is 15.0° C.

Referring to a crystallization apparatus in FIG. 1, the temperature of a crude (meth)acrylic acid solution in the crystallization apparatus may be measured after the crude solution passes through a heat exchange surface and before reaches a liquid reservoir at the bottom of the crystallization apparatus. However, it may be difficult in some cases to measure the temperature of a crude solution at the above-described point or at the lowest part of a heat exchange surface. Thus, in the present invention, as a simpler method, the cooling condition of a crude solution in a crystallization apparatus is recognized from the change in the temperature of the cooling medium discharged from the crystallization apparatus after the crude solution is cooled.

In conventional processes, a (meth) acrylic acid solution is excessively cooled immediately after the solution is supplied into a crystallization apparatus to precipitate (meth) acrylic acid. However, according to such conventional processes, a crystal having adequate quality cannot be obtained, and it is necessary to increase the number of crystallization cycle for obtaining a crystal of satisfactory quality. On the other hand, in the present invention process, first, the temperature of a cooling medium discharged from a crystallization apparatus is stabilized in the range of higher than the solidification point of the crude (meth) acrylic acid solution in a crystallization apparatus and not more than the solidification point plus 5° C. so that the temperature of the crude (meth) acrylic acid solution in the crystallization apparatus is stabilized nearly in the same range.

More specifically, when a crude solution at a relatively high temperature is supplied into a crystallization tube of a crystallization apparatus and time does not pass sufficiently, the temperature of a cooling medium discharged from the crystallization apparatus (the cooling medium temperature at the cooling medium outlet of the crystallization apparatus) is higher than the temperature of the cooling medium supplied to the crystallization apparatus (the cooling medium temperature at the cooling medium inlet of the crystallization apparatus), since the heat of the crude solution is transferred to the cooling medium via a heat-transfer surface. However, when the overall temperature of a crude solution is sufficiently reduced depending on the preset temperature of the cooling medium supplied to a crystallization apparatus and the temperature of the crude solution cyclically-supplied to the crystallization apparatus (the crude solution temperature at the crude solution inlet of the crystallization apparatus) is stabilized, the cooling energy lost at a heat-transfer surface becomes constant and the temperature of the cooling medium discharged from the crystallization apparatus is stabilized. In the present invention, if the temperature of a cooling medium discharged from a crystallization apparatus is stabilized in the range of higher than the solidification point of a crude (meth) acrylic acid solution and not more than the solidification point plus 5° C., the temperature of the crude solution cooled on a heat-exchange surface of the crystallization apparatus is considered to be stabilized in the same temperature range.

The temperature of a cooling medium supplied to a crystallization apparatus (the cooling medium temperature at the cooling medium inlet of the crystallization apparatus) may be appropriately adjusted depending on the changes of the temperature of the cooling medium discharged from the crystallization apparatus (the cooling medium temperature at the cooling medium outlet of the crystallization apparatus) or the temperature of the crude solution discharged from the crystallization apparatus (the crude solution temperature at the crude solution outlet of the crystallization apparatus). For example, if the cooling medium temperature at the cooling medium inlet of the crystallization apparatus is set to be higher than the solidification point of a crude solution, a (meth)acrylic acid crystal having higher purity can be obtained though it may take a long time to sufficiently cool the crude solution and to stabilize the cooling medium temperature at the cooling medium outlet of the crystallization apparatus. On the other hand, for example, the cooling medium temperature at the cooling medium inlet of the crystallization apparatus may be set to be lower than the solidification point of a crude solution at the beginning of the supply of the crude solution, and the cooling medium temperature at the cooling medium inlet of the crystallization apparatus may be adjusted to be higher than the solidification point of the crude solution depending on the changes of the cooling medium temperature at the cooling medium outlet of the crystallization apparatus and the crude solution temperature at the crude solution outlet of the crystallization apparatus so that the part of the crude solution does not coagulate. As a result, it becomes possible to shorten the time necessary to stabilize the cooling medium temperature at the cooling medium outlet of the crystallization apparatus and a more efficient crystallization becomes possible, though the purity of the obtained crystal may be possibly somewhat decreased. When a plurality of crystallization purification cycles are repeated, the cooling medium temperature at the cooling medium inlet of the crystallization apparatus may be gradually increased from below the solidification point of a crude solution at the beginning of the cycles, such as the first cycle, with the objective of shortening the cooling time more than the degree of purification as long as the cooling medium temperature at the cooling medium outlet of the crystallization apparatus is stabilized in the range of not more than the solidification point plus 5° C.

In the present invention, "stabilization" of the temperature of a cooling medium discharged from a crystallization apparatus means that the rate of temperature change of said cooling medium per unit time becomes not more than 1.0° C./min.

2. Supercooling Step

In the present invention, after the temperature of the cooling medium discharged from a crystallization apparatus is stabilized within the above-described temperature range, the preset temperature of the cooling medium supplied to the crystallization apparatus is lowered to less than the solidification point of a crude solution so that the temperature of the crude solution within the crystallization apparatus is decreased to lower than the solidification point and the crude solution is put in a clear supercooled condition.

In general, a solution of a chemical compound immediately before crystallization is in a supercooled state. However, when a solution is rapidly cooled down to less than the solidification point thereof, a clear supercooled state cannot be frequently confirmed in many cases. On the other hand, in the present invention, a clear supercooled state of a crude (meth) acrylic acid solution is achieved by cooling as much as possible and stabilizing the crude solution in the range that (meth)acrylic acid does not precipitate and then further cooling the crude solution down to lower than the solidification point thereof.

More specifically, a crude solution is cooled in a crystallization apparatus until the temperature of the cooling medium discharged from the crystallization apparatus is stabilized in the above-described preset range, and then, the temperature of the cooling medium supplied to the crystallization apparatus is set to be lower than the solidification point of the crude solution by not less than 1° C. When said temperature is set to be lower than the solidification point of the crude solution by not less than 1° C. after the above-described preliminary cooling, it is possible that the crude solution is put in a clear supercooled state. In the present invention, the term. "a supercooled state" means that the temperature of a crude (meth)

acrylic acid solution is temporarily lowered to not more than the solidification point thereof minus 0.1° C. without forming a (meth)acrylic acid crystal.

In the present invention, it is preferred that the temperature of the above-mentioned cooling medium to put a crude solution in a supercooled state is set to be lower than the solidification point of the crude solution by not less than 1° C. and yet not more than 10° C. As mentioned above, a crude solution can be put in a supercooled state by cooling the solution down to less than the solidification point. The present inventors found that a highly pure (meth)acrylic acid crystal can be obtained more surely by setting the temperature of the above-mentioned cooling medium set to be lower than the solidification point of the crude solution by not less than 1° C. and yet not more than 10° C. for rapidly cooling the crude solution and putting the crude solution in a supercooled state.

3. Crystallization Step

In the present invention process, a crude (meth)acrylic acid solution is put in a supercooled state, and then (meth)acrylic acid is crystallized. In case of using a dynamic type crystallization apparatus shown in FIG. 1, there is no necessity for fundamentally special handling. The (meth)acrylic acid in such a apparatus is automatically crystallized once a crude solution is put in a supercooled state, since the crude solution is constantly flowing.

A highly pure (meth)acrylic acid crystal can be obtained by the present invention process. The reason why the purity of a crystal can be improved by the present invention process is unclear; however, the present inventor believes that a highly pure crystal is firstly produced under a clear supercooled condition, since the quality of a crystal changes significantly depending on the initial precipitation conditions, and then, (meth)acrylic acid, which is the target chemical compound, is selectively crystallized out on the highly pure crystal nuclei.

In the crystallization apparatus shown in FIG. 1, a (meth)acrylic acid crystal precipitates on the heat-transfer surface of the interior side of a crystallization tube. The liquid film flow of a cooled crude solution is supplied to the (meth)acrylic acid crystal precipitated through a supercooled state; as a result, the (meth)acrylic acid crystal grows. After (meth)acrylic acid is sufficiently crystallized out from a crude solution, a general posttreatment can be optionally carried out.

For example, when there is an impurity in the surface area of a crystal or if an impurity adheres to a crystal surface, a sweating step may be optionally carried out. Specifically, a crystal surface optionally partially melted for removing a impurity. In such a case, a crystal surface is partially melted at a suitable temperature by replacing a cooling medium with a heating medium. After a highly pure (meth)acrylic acid crystal is obtained, the crystal may be melted by raising the temperature of a heating medium to get the crystal out of a crystallization apparatus. In order to obtain a (meth)acrylic acid crystal of higher purity, crystallization purification may be optionally repeated by supplying a melted (meth)acrylic acid to a crystallization apparatus again.

EXAMPLES

Hereinafter, the present invention is described in detail with Examples. However, the present invention is not limited to the Examples in any way, and it is possible to carry out the present invention according to the Examples with an additional appropriate change within the range of the above descriptions and the following descriptions. Such a change is also included in the technical scope of the present invention.

Example 1

Beginning Crystallization Purification of Acrylic Acid (1) Crude Acrylic Acid Solution Propylene was subjected to a gas-phase catalytic oxidation reaction in a reactor. The produced reaction gas was supplied into a collection tower and contacted with a collecting liquid to obtain a crude acrylic acid solution. The crude solution was gotten out from the bottom of the collection tower. The composition of said crude acrylic acid solution was as follows: acrylic acid: 90.0 mass %, water: 3.2 mass %, acetic acid: 1.9 mass %, maleic acid: 0.6 mass %, acrylic acid dimer: 1.5 mass %, furfural: 0.07 mass %, benzaldehyde: 0.27 mass %, formaldehyde: 0.06 mass %, hydroquinone: 0.1 mass %, and other impurities: 2.3 mass %. The solidification point of said solution was measured as 8.0-8.5° C.

(2) Preliminary Cooling Step

The crude acrylic acid solution obtained in the above (1) was supplied to a tank, and the temperature thereof was adjusted to 22° C. Then, 55 kg of the crude solution was supplied to the bottom of a pilot-scale falling liquid film crystallization apparatus as shown in FIG. 1. The crystallization tube inside said crystallization apparatus was a metal tube with a diameter of 70 mm and a length of 18 m. In said crystallization apparatus, a crude solution was transferred to the top of the tube using a circulation pump and the crude solution could flow as a falling film along the wall surface of the crystallization tube. Said crystallization apparatus was equipped with thermometers at the medium inlet portion and outlet portion, and at the portion immediately before the crystallization tube of the crude solution supply tube and the portion immediately after the crystallization tube. Said crude solution was drawn from the bottom, and circulation was begun at a supply rate of 0.34 m$^3$/hr. Additionally, the supply of a cooling medium set to the range of 25-30° C. was begun at a supply rate of 0.82 m$^3$/hr to the same crystallization apparatus.

First, the temperature of the cooling medium supplied to the crystallization apparatus was lowered down to 5° C. The difference of the cooling medium temperature from the solidification point of the crude solution became −3 to −3.5° C. As a result, the temperature of the crude solution at the outlet also dropped, the temperature of the crude solution at the outlet and the temperature of the cooling medium at the outlet became approximately the same about 3 minutes after the temperature of the cooling medium was lowered, and the temperature of the cooling medium at the outlet changed only from 10° C. to 9° C. in a 3-minute period and was stabilized.

(3) Supercooling Step to Crystallization Step

Next, the temperature of the cooling medium at the inlet was lowered down to 1.5° C. The difference of the cooling medium temperature from the solidification point of the crude solution became −9.5 to −10° C. As a result, after the temperature of the crude solution at the outlet temporarily dropped to 7.5° C., the temperature rose to the above-described solidification point, and then, the solidification point gradually decreased due to the concentration of impurity and the lowering of acrylic acid purity.

Once the temperature of the cooling medium at the inlet was decreased to −1.5° C., and further gradually lowered. The circulation of the crude solution was terminated when the amount of the crude solution was reduced to 12.2 kg, and the crude solution was withdrawn from the bottom of the crystallization apparatus. Next, after a sweating step was carried out by replacing the cooling medium with a heating medium of a temperature close to the solidification point, the melted portion was withdrawn from the bottom of the crystallization apparatus. The crystal was completely melted by raising the temperature of the heating medium, and the melted acrylic acid was withdrawn from the bottom of the crystallization apparatus.

The content ratio of impurity in the obtained acrylic acid was measured by gas chromatography system (manufactured by Shimadzu Corp.); as a result, the content amount of acetic acid was reduced to 0.95 mass %. In addition, the ratio was also measured by liquid chromatography system (manufactured by Shimadzu Corp.); as a result, the hydroquinone content was reduced to 0.025 mass %.

Example 2

Acrylic acid was produced in the same condition as Example 1 except that the temperature of the cooling medium at the inlet was changed to −5.0° C. in the supercooling step. The difference of the cooling medium temperature from the solidification point of the crude solution was −13 to −13.5° C. In the case, the temperature of the crude acrylic acid solution at the outlet temporarily dropped down to 7.5° C. due to a supercooled state. Thereafter, although the value measured on a pressure meter with which the crystallization apparatus was equipped was increased slightly during the crystallization and it was observed that the upper portion of the crystallization tube seemed to be somewhat blocked, it was possible to operate the production up to the end.

The purity of the obtained acrylic acid was measured in the same manner as Example 1; as a result, the purity was slightly decreased. Specifically, the acetic acid content was 1.06 mass % and hydroquinone content was 0.028 mass %. The reason is believed to be a more sudden progression of the crystallization by changing the temperature of the cooling medium at the inlet from −1.5° C. to −5° C., so that the condition of the crystal adhering to the crystallization tube was deteriorated.

Comparative Example 1

Acrylic acid was produced in the same condition as Example 1 except that the temperature of the cooling medium for cooling the crude acrylic acid solution was consistently 1° C., and the circulation of the crude acrylic acid solution was begun from a state where the temperature of the crystallization tube of the crystallization apparatus was not more than the solidification temperature of the crude acrylic acid. The difference of the cooling medium temperature from the solidification point of the crude solution was −7 to −7.5° C. In the case, no clear supercooled state was observed and the temperature of the crude solution merely continued to drop down to the solidification point, since the temperature of the heat-transfer surface of the crystallization tube was not more than the solidification point and crystallization began immediately after circulation of the crude acrylic acid solution was begun.

The purity of the obtained acrylic acid was measured in the same manner as Example 1; as a result, the purity was decreased. Specifically, the acetic acid content was 1.27 mass % and hydroquinone content was 0.033 mass %.

The results of the above Examples 1-2 and Comparative Example 1 are shown in Table 1

TABLE 1

|  | Example 1 | Example 2 | Comparative Example 1 |
|---|---|---|---|
| Crude solution solidification point | 8-8.5° C. | 8-8.5° C. | 8-8.5° C. |
| Temperature of the cooling medium during pre-cooling (difference from the crude solution solidification point) | 5° C. (−3 to −3.5° C.) | 5° C. (−3 to −3.5° C.) | 1° C. (−7 to −7.5° C.) |
| Temperature of the cooling medium during crystallization (difference from the crude solution solidification point) | −1.5° C. (−9.5 to −10° C.) | −5.0° C. (−13 to −13.5° C.) | 1° C. (−7 to −7.5° C.) |
| Supercooled state | Observed | Observed | Could not be observed |
| Acetic acid (impurity) content | 1.9% → 0.95% | 1.9% → 1.06% | 1.9% → 1.27% |
| Hydroquinone (impurity) content | 0.1% → 0.025% | 0.1% → 0.028% | 0.1% → 0.033% |
| Remarks |  | Acrylic acid purity slightly decreased Crystallization tube seemed to be somewhat blocked | Acrylic acid purity decreased |

As the above results, the purity of the obtained acrylic acid was low when no supercooled state was observed in the crude acrylic acid solution by measuring the temperature of the crude acrylic acid solution immediately after the crystallization tube outlet and the temperature of the cooling medium at the outlet of the crystallization apparatus. On the other hand, the purity of the acrylic acid was high when a clear supercooled state was observed. In addition, the purity was clearly higher when the cooling condition for a supercooled state was mild. In contrast, the concentration of impurity became higher when no clear supercooled state was observed, and it was necessary to increase the number of purification cycles for reducing the impurity amount to the presumed amount.

Example 3

Beginning Crystallization Purification of Acrylic Acid (1) Melted Acrylic Acid

Propylene was subjected to a gas-phase catalytic oxidation reaction in a reactor. The produced reaction gas was supplied into a collection tower and contacted with a collecting liquid to obtain a crude acrylic acid solution. The crude solution was gotten out from the bottom of the collection tower. The crude acrylic acid was purified several times using a crystallization apparatus under a general condition. The amount of the impurity included in the obtained acrylic acid was 1500 ppm by mass of acrylic acid and 1 ppm by mass of hydroquinone. The solidification point of the melted liquid was measured as 13-14° C.

(2) Preliminary Cooling Step

The melted acrylic acid obtained in the above (1) was supplied to a tank, and the temperature thereof was adjusted to 22° C. Then, 68.6 kg of the melted acrylic acid was supplied to the bottom of a falling liquid film crystallization apparatus as shown in FIG. 1. Said crystallization apparatus was equipped with thermometers at the medium inlet portion and outlet portion, and at the portion immediately before the crystallization tube and the portion immediately after the crystallization tube. Said melted acrylic acid was drawn from the bottom, and circulation was begun at a supply rate of 0.34 m$^3$/hr. Additionally, the supply of a cooling medium set to the range of 25-30° C. was begun at a supply rate of 0.82 m$^3$/hr to the same crystallization apparatus.

First, the temperature of the cooling medium supplied to the crystallization apparatus was lowered down to 10° C. The difference of the cooling medium temperature from the solidification point of the crude solution became −3 to −4° C. As a result, the temperature of the melted acrylic acid at the outlet also dropped, the temperature of the melted acrylic acid at the outlet and the temperature of the cooling medium at the outlet became approximately the same about 3 minutes after the temperature of the cooling medium was lowered, and the temperature of the cooling medium at the outlet changed only from 15° C. to 14° C. in a about 2-minute period and was stabilized.

(3) Crystallization Step from Supercooling Step

Next, the temperature of the cooling medium at the inlet was lowered down to 7° C. The difference of the cooling medium temperature from the solidification point of the crude solution became −6 to −7° C. As a result, after the temperature of the melted acrylic acid at the outlet temporarily dropped to 12.8° C., the temperature rose to the above-described solidification temperature, and then, the solidification point gradually decreased due to the concentration of impurity and the lowering of acrylic acid purity.

Once the temperature of the cooling medium at the inlet was decreased to 7° C., and further gradually lowered. The circulation of the crude solution was terminated when the amount of the melted acrylic acid was reduced to 20.2 kg, and the melted acrylic acid was withdrawn from the bottom of the crystallization apparatus. Next, after a sweating step was carried out by replacing the cooling medium with a heating medium of a temperature close to the solidification point, the melted portion was withdrawn from the bottom of the crystallization apparatus. The crystal was completely melted by further raising the temperature of the heating medium, and the melted acrylic acid was withdrawn from the bottom of the crystallization apparatus.

The content ratio of impurity in the obtained acrylic acid was measured by gas chromatography system (manufactured Shimadzu Corp.); as a result, the acetic acid content was decreased to 535 ppm by mass. In addition, the ratio was also measured by liquid chromatography system (manufactured by Shimadzu Corp.); as a result, the hydroquinone content was reduced to less than 0.1 ppm by mass.

Example 4

Acrylic acid was produced in the same condition as Example 3 except that the temperature of the cooling medium at the inlet was changed to 2° C. in the supercooling step. The difference of the cooling medium temperature from the solidification point of the crude solution was −11 to −12° C. In the case, the temperature of the crude acrylic acid solution at the outlet temporarily dropped down to 12.8° C. due to a supercooled state. Thereafter, although the value measured on a pressure meter with which the crystallization apparatus was equipped was slightly increased during the crystallization and it was observed that the upper portion of the crystallization tube seemed to be somewhat blocked, it was possible to operate the production up to the end.

The purity of the obtained acrylic acid was measured in the same manner as Example 3; as a result, the purity was slightly decreased in comparison with Example 3. Specifically, the acetic acid content was 545 ppm by mass. The reason is believed to be a more sudden progression of the crystallization by changing the temperature of the cooling medium from 7° C. to 2° C. in the supercooling step, so that the condition of the crystal adhering to the crystallization tube was deteriorated. On the other hand, the measured content of hydroquinone was unchanged.

Comparative Example 2

Acrylic acid was produced in the same condition as Example 3 except that the temperature of the cooling medium for cooling the crude acrylic acid solution was consistently 7.5° C., and the circulation of the crude acrylic acid solution was begun from a state where the temperature of the crystallization tube of the crystallization apparatus was not more than the solidification temperature of the crude acrylic acid. The difference of the cooling medium temperature from the solidification point of the crude solution was −5.5 to −6.5° C. In the case, no clear supercooled state was observed and the temperature of the crude solution merely continued to drop down to the solidification point, since the temperature of the heat-transfer surface of the crystallization tube was not more than the solidification point and crystallization began immediately after circulation of the crude acrylic acid solution was begun.

The purity of the obtained acrylic acid was measured in the same manner as Example 3; as a result, the purity was decreased in comparison with Example 3. Specifically, the acetic acid content was 600 ppm by mass and hydroquinone content was 0.1 ppm by mass.

Example 5

Beginning the Crystallization Purification of Acrylic Acid (1) Preliminary Cooling Step The melted acrylic acid obtained by the same condition as the above Example 3(1) was supplied to a tank, and the temperature thereof was adjusted to 22° C. Then, 68.6 kg of the melted acrylic acid was supplied to the bottom of a falling liquid film crystallization apparatus as shown in FIG. 1. Said crystallization apparatus was equipped with thermometers at the medium inlet portion and outlet portion, and at the portion immediately before the crystallization tube and the portion immediately after the crystallization tube. Said melted acrylic acid was drawn from the bottom, and circulation was begun at a supply rate of 0.34 m$^3$/hr. Additionally, the supply of a cooling medium set to the range of 25-30° C. was begun at a supply rate of 0.82 m$^3$/hr to the same crystallization apparatus.

First, the temperature of the cooling medium supplied to the crystallization apparatus was lowered down to 15° C. The difference of the cooling medium temperature from the solidification point of the crude solution became +1 to +2° C. As a result, the temperature of the melted acrylic acid at the outlet also dropped, the temperature of the melted acrylic acid at the outlet and the temperature of the cooling medium at the outlet became approximately the same about 3 minutes after the temperature of the cooling medium was lowered, and the temperature of the cooling medium at the outlet changed only from 17.5° C. to 17.0° C. in a about 3-minute period and was stabilized.

(2) Crystallization Step from Supercooling Step

Next, the temperature of the cooling medium at the inlet was lowered at a lowering temperature rate of 0.8° C./min. As a result, after the temperature of the melted acrylic acid at the outlet temporarily dropped to 12.8° C. when the temperature of the cooling medium at the inlet became 9° C., the melted acrylic acid temperature rose to the above-described solidification temperature, and then, the solidification point gradually decreased due to the concentration of impurity and the lowering of acrylic acid purity.

The temperature of the cooling medium was gradually lowered. The circulation of the crude solution was terminated when the amount of the melted acrylic acid was reduced to 20.2 kg, and the melted acrylic acid was withdrawn from the bottom of the crystallization apparatus. Next, after a sweating step was carried out by replacing the cooling medium with a heating medium of a temperature close to the solidification point, the melted portion was withdrawn from the bottom of the crystallization apparatus. The crystal was completely melted by further raising the temperature of the heating medium, and the melted acrylic acid was withdrawn from the bottom of the crystallization apparatus.

The content ratio of impurity in the obtained acrylic acid was measured by gas chromatography system (manufactured Shimadzu Corp.); as a result, the acetic acid content was decreased to 500 ppm by mass. In addition, the ratio was also measured by liquid chromatography system (manufactured by Shimadzu Corp.); as a result, the hydroquinone content was reduced to less than 0.1 ppm by mass.

The results of the above Examples 3-5 and Comparative Example 2 are shown in Table 1.

solutions. Specifically, the concentration of impurity in the obtained acrylic acid was high when no supercooled state was observed in the crude acrylic acid solution; on the other hand, the concentration of impurity in the obtained acrylic acid was low when a clear supercooled state was observed. In addition, the purity was clearly higher when the cooling condition for a supercooled state was mild.

INDUSTRIAL APPLICABILITY

According to the present invention process, even from a crude (meth)acrylic acid solution which contains many impurities and of which component varies drastically depending on a reaction condition, such as one derived from a gas-phase catalytic oxidation reaction, it is possible to obtain highly pure (meth)acrylic acid stably and efficiently by using crystallization. Accordingly, since the present invention process is suitable for large-scale industrial production of (meth)acrylic acid, the process is extremely useful from an industrial perspective.

The invention claimed is:

1. A process for production of (meth)acrylic acid, comprising the steps of:
cooling a crude (meth)acrylic acid solution in a crystallization apparatus until the temperature of a cooling medium discharged from the crystallization apparatus is stabilized in the range of higher than the solidification point of the crude (meth)acrylic acid solution in the crystallization apparatus and not more than the solidification point plus 5° C., wherein the temperature of the cooling medium is stabilized without forming crystals of (meth)acrylic acid in the (meth)acrylic acid solution;
then bringing the crude (meth)acrylic acid solution in the crystallization apparatus to a supercooled condition by setting the temperature of a cooling medium supplied to the crystallization apparatus to be lower than the solidification point of the crude (meth)acrylic acid solution by not less than 1° C., wherein the crude (meth)acrylic acid solution is brought to a supercooled condition without forming crystals of (meth)acrylic acid; and

TABLE 2

|  | Example 3 | Example 4 | Comparative Example 2 | Example 5 |
|---|---|---|---|---|
| Crude solution solidification point | 13-14° C. | 13-14° C. | 13-14° C. | 13-14° C. |
| Temperature of the cooling medium during pre cooling (difference from the crude solution solidification point) | 10° C. (−3 to −4° C.) | 10° C. (−3 to −4° C.) | 7.5° C. (−5.5 to −6.5° C.) | 15° C. (+1 to +2° C.) |
| Temperature of the cooling medium during crystallization (difference from the crude solution solidification point) | 7° C. (−6 to −7° C.) | 2° C. (−11 to −12° C.) | 7.5° C. (−5.5 to −6.5° C.) | 9° C. (−4 to 5° C.) |
| Supercooled state | Observed | Observed | Could not be observed | Observed |
| Acetic acid (impurity) content | 1500 → 535 (ppm) | 1500 → 545 (ppm) | 1500 → 600 (ppm) | 1500 → 500 (ppm) |
| Hydroquinone impurity) content | 1 → <0.1 (ppm) | 1 → <0.1 (ppm) | 1 → 0.1 (ppm) | 1 → <0.1 (ppm) |
| Remarks |  | Acryitc acid purity slightly decreased Crystallization tube seemed to be somewhat blocked | Acrylic acid purity decreased |  |

As the above results, the same result as the Examples 1-2 and Comparative Example 1 was obtained in also the cases where the solidification point were different due to the difference of the acrylic acid concentrations of crude acrylic acid solutions.

crystallizing (meth)acrylic acid from the crude (meth) acrylic acid solution.

2. The process according to claim 1, wherein the temperature of the cooling medium supplied to the crystallization apparatus and used for bringing the crude (meth)acrylic acid solution to a supercooled condition is set to be lower than the solidification point of the crude (meth)acrylic acid solution by not less than 1° C. and yet not more than 10° C.

3. The process according to claim 1, wherein a falling liquid film type crystallization apparatus is used as the crystallization apparatus.

4. The process according to claim 2, wherein a falling liquid film type crystallization apparatus is used as the crystallization apparatus.

* * * * *